United States Patent [19]

Audibert et al.

[11] 4,158,052

[45] Jun. 12, 1979

[54] OIL-FREE ADJUVANT COMPOSITIONS CONTAINING N-ACETYL-MURAMYL-L-ALANYL-D-ISO-GLUTAMINE

[75] Inventors: Françoise Audibert, Neuilly; Louis Chedid, Paris; Pierre Lefrancier, Bures sur Yvette; Jean Choay, Paris; Edgar Lederer, Sceaux, all of France

[73] Assignee: Agence Nationale de Valorisation de la Recherche (ANVAR), Neuilly-sur-Seine, France

[21] Appl. No.: 624,994

[22] Filed: Oct. 22, 1975

Related U.S. Application Data

[63] Continuation-in-part of Ser. No. 516,991, Oct. 22, 1974.

[30] Foreign Application Priority Data

Sep. 26, 1975 [FR] France .................................. 75 29624

[51] Int. Cl.² ..................... A61K 39/02; A61K 39/04; A61K 37/02

[52] U.S. Cl. ......................................... 424/45; 424/88; 424/89; 424/92; 424/177; 424/180

[58] Field of Search .................. 424/177, 180, 88, 89, 424/92, 45

[56] References Cited

PUBLICATIONS

Petit et al.—Chem. Abst. Vol. 79(1973), p. 64476y.
Kotani et al.—Biken Journal, vol. 18, (1975) pp. 105–111.

*Primary Examiner*—Sam Rosen
*Attorney, Agent, or Firm*—Weiser, Stapler & Spivak

[57] ABSTRACT

The invention pertains to drug oil-free compositions, notably aqueous injectable compositions acting as non-specific adjuvants to stimulate in a host the immunitary responses to different antigens. The active principle of these oil-free compositions is N-acetyl-muramyl-L-alanyl-D-isoglutamine.

31 Claims, No Drawings

OIL-FREE ADJUVANT COMPOSITIONS CONTAINING N-ACETYL-MURAMYL-L-ALANYL-D-ISOGLUTAMINE

This application is a continuation-in-part of copending application Ser. No. 516,991, filed Oct. 22, 1974, entitled WATER SOLUBLE AGENTS EFFECTIVE AS IMMUNOLOGICAL ADJUVANTS FOR STIMULATING IN THE HOST THE IMMUNE RESPONSE TO VARIOUS ANTIGENS AND COMPOSITIONS, NOTABLY VACCINES CONTAINING SAID WATER SOLUBLE AGENTS.

The invention relates to oil-free drug compounds, acting as immunological adjuvants to stimulate a host's immune response to different sorts of antigens. More particularly, the invention concerns drug compounds of said type, capable of reinforcing and enhancing the action of weak immunogens.

More particularly, the invention relates to adjuvant drug compounds, likely to be used for immunizing man and warm blood animals against bacteria, viral and parasitic infections and also against various tissue antigens having a normal or pathological origin, among others tumors.

Adjuvant agents have already been described in French Pat. No. 71 41610 filed Nov. 19, 1971, on which is based U.S. patent application Ser. No. 307,614, now issued as U.S. Pat. No. 4,036,953 on July 17, 1977, of which Ser. No. 806,987 is a copending divisional application. which are obtained more particularly by a process consisting in cultivating a strain of Mycobacteria, Nocardia cells or related micro-organisms, collecting the cells of the cultivated strains, causing their disruption and recovering the disrupted cell-walls (for instance by differential centrifugation) and then separating and eliminating the waxes, free lipids, proteins and nucleic acids, causing the digestion of the delipidated substance originating from cell-walls and having previously been suspended in an aqueous medium, by a murolytic enzyme, such as lysozyme, eliminating the solid residue and collecting the aqueous fraction which contains aforesaid soluble agents, further purification of which is obtained, i.e. by filtration of said aqueous fraction through a molecular sieve of the SEPHADEX type (polydextran gel) or alike.

As already indicated in this patent, the active part of these adjuvant agents consisted essentially of an oligomer, the monomer unit of which fairly corresponds to that of the cell-walls polymers of mycobacteriae or Nocardia cells from which they originate.

As has been demonstrated in this patent, the hydrosoluble adjuvant agents of the type referred to, show a noteworthy adjuvant activity when administered in the form of an aqueous-oily emulsion to test animals. They have also proved to show a certain adjuvant activity when administered in the form of an aqueous solution (test of N. K. Jerne et al. described in "Cell bound antibodies" ed. B. Ames and H. Koprovski Wistar Institute Press, Philadelphia, 1963). However, Jerne's test concerns but locally formed antibodies; it is not representative of a non specific immunostimulant activity tending to increase the rate of circulating antibodies; still these adjuvant agents contained in an aqueous solution do not result in an increase in vivo of the rate of circulating antibodies (present in the serum).

Under such conditions, it appears that the adjuvant activity of aqueous solutions containing the agents described in the above mentioned application could, at best, have but a very reduced therapeutical interest; subsequent studies of these agents in view of their therapeutical applications have thus been carried out, using an aqueous-oily emulsion. Particularly, the same applied as concerns different products of ever-decreasingly low molecular masses, which have been extracted from above adjuvants or derivate therefrom.

As disclosed in the French patent application No. 7,337 806 filed Oct. 23, 1973 (corresponding in part to U.S. patent application Ser. No. 516,991, referred to herein above), the adjuvant activity of thus obtained preparations when administered within an aqueous-oily emulsion, had been attributed to the presence in these preparations of soluble fragments of the peptidoglycans contained in the cell walls of bacteria treated by the above process. More particularly, the above application described hydrosoluble adjuvant agents consisting of peptidoglycan fragments formed of polysaccharides-polypepetides of low molecular weight, particularly of oligosaccharides-oligopeptides, the polysaccharide part of which consisted in N-acetyl-glucosamine units, on the one hand, and N-acyl-muramic acid (more particularly N-glycolyl-muramic acid, on the other hand.

As has been ascertained in French Patent No. 74 22909 filed on July 1, 1974 (corresponding in part to U.S. patent application Ser. No. 516,991, referred to herein above), the N-acetyl-glucosamine portion was not necessary to the adjuvant action of agents containing peptidoglycane soluble fragments. Pending U.S. patent application Ser. No. 516,991 to Adam, Audibert et al is based on said two above-referred to French patent applications, namely French application No. 73.37.806 filed Oct. 23, 1973 and No. 74.22.909 filed July 1, 1974. Particularly, this application describes a synthetic hydrosoluble adjuvant agent consisting of N-acetyl-muramic acid carrying a dipeptide group, the latter being preferably formed of L-alanine, directly linked to the N-acetyl-muramic acid, and of D-glutamic acid, the latter being preferably the amid derivative (on the α-carboxyl group). The product considered was thus, in the latter case, the so-called "N-acetyl-muramyl-L-alanyl-D-isoglutamine" (Mur-NAc-L-Ala-D-Glu-α-NH$_2$) of formula:

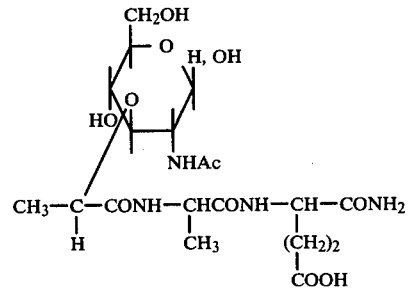

This product is also identified as follows: 2-(2-acetamido-2-deoxy-3-O-D-glucopyranosyl)-D-propionyl-L-alanyl-D-α-isoglutamine.

Like the adjuvant agents formed of more important molecules, the constitution of which has been recalled hereabove, the Mur-NAc-L-Ala-D-Glu-α-NH$_2$ has exhibited an excellent adjuvant activity when administered to test animals in the form of an aqueous-oily emulsion.

However, the necessity of resorting to aqueous-oily emulsions in order to bring out the efficient adjuvant action of agents of the type referred to, entails many drawbacks. Most of the oils used, up to the present, for the preparation of such emulsions, are formed of paraffin or analogous oils, which cannot be metabolized. Moreover, the emulsifying agents needed for stabilizing said emulsions, for instance those known under the designation "ARLACEL" do not exhibit the desirable inocuity. All aforesaid drawbacks have thus considerably reduced the use of the hydrosoluble adjuvant agents described hereabove in therapy, particularly human therapy.

In order to overcome, at least partly, such drawbacks, it has been proposed to prepare aqueous-oily emulsions, using vegetable oils. Various experiences have been tempted that way, but most authors have stumbled against the problem of stabilizing these emulsions.

The invention described in French patent application No. 75 04003, filed Feb. 7, 1975, has substantially improved the situation. It describes a stabilized water-vegetable oil emulsion, usable as a vehicle for administering agents of the type referred to, especially the above mentioned N-acetyl-muramyl-L-alanyl-D-isoglutamine. Nevertheless, this invention, though achieving an important improvement, does not remove the need for a water-oil emulsion.

This invention derives from an essentially important discovery, i.e.: against any expectation, N-acetyl-muramyl-L-alanyl-D-isoglutamine exhibits a noteworthy non specific adjuvant activity, even when administered to the host in the form of an oil-free aqueous solution. Taking into account its chemical relationship with previous adjuvants, formed of the bacterial extracts referred to hereabove, it was quite unforeseeable that N-acetyl-muramyl-L-alanyl-D-isoglutamine should be capable of exerting such an action, more especially of enhancing the production of circulating antibodies in vivo without having recourse, in the administration medium, to an oil, either of mineral or vegetal origin. This discovery of the adjuvant properties of oil-free compositions—especially aqueous solutions—represents an essential advance in the field of therapeutical uses, especially for men, of drugs having a non specific adjuvant activity with respect to immunity. As a matter of fact, N-acetyl-muramyl-L-alanyl-D-isoglutamine, which is not only soluble but also has been discovered to be active in aqueous solution, can exert its activity in physiological serums, which was not the case for the previously known non specific adjuvants of immunity.

It has been moreover observed that, contrarily to the previously described hydrosoluble adjuvant agents, N-acetyl-muramyl-L-alanyl-D-isoglutamine induced no sensitization of the host, either against N-acetyl-muramyl-L-alanyl-D-isoglutamine itself, or against various previously cited adjuvants, prepared from mycobacteria or analogous. This sensitization, induced by the previously described hydrosoluble adjuvants, appears in the form of hypersensitivity reactions of tuberculinic type on subjects having previously been put into contact with the adjuvants themselves or with mycobacterial germs or extracts.

Thus, N-acetyl-muramyl-L-alanyl-D-isoglutamine, does not constitute a sensitizer; in other words, it has no immunogenic properties, particularly, it does not bring about any reaction on subjects, either sensitive or sensitized to tuberculinic bacilla. Therefore, it has not an antigenic structure of the same type as that of previous adjuvants. N-acetyl-muramyl-L-alanyl-D-isoglutamine is therefore in that respect perfectly harmless for subjects which have previously been contacted, either with the product itself or with the above mentioned previous adjuvants, or with mycobacteria or analogous.

The invention derives also from the essential discovery that, against any expectation, the substance constituted by N-acetyl-muramyl-L-alanyl-D-glutamic acid, has a noteworthy non specific adjuvant activity, when administered to an host under the form of an oil-free aqueous solution. N-acetyl-muramyl-L-alanyl-D-glutamic acid, which may be designated by the abbreviated form:

corresponds to the following formula:

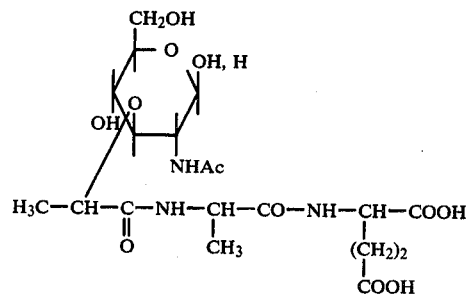

To identify said substance, one may have recourse to official nomenclature. It is then called: 2-(2-acetamido-2-deoxy-3-O-D-glucopyranosyl)-D-propionyl-L-alanyl-D-glutamic acid.

Taking into account its chemical relationship with previous adjuvants, constituted by bacterial extracts, it was quite unforeseeable that N-acetyl-muramyl-L-alanyl-D-glutamic acid should be able of exerting such an action, more especially of enhancing the production of circulating antibodies in vivo without having recourse, in the administration medium, to an oil, either of mineral or vegetal origin. This discovery of the adjuvant properties of oil-free compositions—especially aqueous solutions—represents an essential advance in the field of therapeutical uses, especially for men, of drugs having a non specific adjuvant activity with respect to immunity. As a matter of fact, N-acetyl-muramyl-L-alanyl-D-isoglutamine, which is not only soluble but has also been discovered to be active in aqueous solution, can exert its activity in physiological serums, which was not the case for the previously known non specific adjuvants of immunity.

The non specific adjuvant activity of said substance in oil-free aqueous solution is all the more noteworthy as the same substance, when administered within an aqueous-oily emulsion, presents but a much lower activity. This reversal of the intensities of the properties of adjuvant activity according to the nature of the medium used was, of course, quite unexpected, considering what was already known of previous adjuvants, the nature of which has been recalled hereabove.

It has been moreover observed that, contrary to the previously described hydrosoluble adjuvant agents, N-acetyl-muramyl-L-alanyl-D-isoglutamine induced no sensitization of the host, either against N-acetyl-muramyl-L-alanyl-D-isoglutamine itself, or against various previously cited adjuvants, prepared from mycobacteria, Nocardia or analogous. This sensitization, induced by the previously described hydrosoluble adjuvants, appears in the form of hypersensitivity reactions of tuberculinic type on subjects having previously been put into contact with the adjuvants themselves or with mycobacterial germs or extracts.

Thus, N-acetyl-muramyl-L-alanyl-D-isoglutamine, does not constitute a sensitizer; in other words, it has no immunogenic properties, particularly, it does not bring about any reaction on subjects, either sensitive or sensitized, to tuberculinic bacilla. Therefore, it has not an antigenic structure of the same type as that of previous adjuvants. N-acetyl-muramyl-L-alanyl-D-isoglutamine is therefore, in that respect, perfectly harmless for subjects which have previously been contacted, either with the product itself or with the above mentioned previous adjuvants, or with mycobacteria or analogous.

Thus, the invention relates to oil-free compositions containing N-acetyl-muramyl-L-alanyl-D-isoglutamine or N-acetyl-muramyl-L-alanyl-D-glutamic acid, associated with a pharmaceutically acceptable vehicle. By oil-free compositions is more particularly meant compositions free of an oil which is liquid at ambient temperature, say at 25° C.

The invention relates particularly to oil-free solutions containing N-acetyl-muramyl-L-alanyl-D-isoglutamine or N-acetyl-muramyl-L-alanyl-D-glutamic acid, more especially sterile or sterilizable solutions, injectable or able to be used, more especially extemporaneously, for the preparation of injectable solutions. It particularly concerns physiological aqueous solutions, more especially isotonic ones, such as saline or glucose solutions, of one of these compounds. It is to be understood that these examples infer no limitation as to the definition of physiologically acceptable products which may be used to constitute isotonic injectable solutions.

However, the invention concerns also N-acetyl-muramyl-L-alanyl-D-isoglutamine or N-acetyl-muramyl-L-alanyl-D-glutamic acid solutions in distilled water or in water totally free from products such as mineral salts which, upon evaporation, leave a solid residue, such solutions being able to be used subsequently for the preparation of vaccines.

The invention also relates to compositions or solutions of the above indicated type in which N-acetyl-muramyl-L-alanyl-D-isoglutamine or N-acetyl-muramyl-L-alanyl-D-glutamic acid are associated to a vaccinating antigen, particularly to a weak immunogen, in order to reinforce the host's organism capacity to produce antibodies against this antigen.

The invention relates also to N-acetyl-muramyl-L-alanyl-D-isoglutamine or N-acetyl-muramyl-L-alanyl-D-glutamic acid as a lyophilised product this lyophilisate possibly containing also a vaccinating antigen mixed with N-acetyl-muramyl-L-alanyl-D-isoglutamine or N-acetyl-muramyl-L-alanyl-D-glutamic acid.

The invention relates also to oil-free pharmaceutical compositions containing the adjuvant agent, more especially injectable aqueous vaccinating compositions containing, in addition to the adjuvant, an active principle of vaccine, these pharmaceutical compositions being able to be administered by sub-cutaneous, intradermic or intramuscular injections, or still by scarification.

It also relates to pharmaceutical compositions which may be administered by other routes, i.e. orally or rectally, or under the form of aerosols intended for entering into contact with mucous membranes, more especially, ocular, nasal or vaginal membranes.

Consequently, it concerns also pharmaceutical compositions in which N-acetyl-muramyl-L-alanyl-D-isoglutamine or N-acetyl-muramyl-L-alanyl D-glutamic acid are associated to solid or liquid pharmaceutically acceptable vehicles, suitable for the constitution of forms intended for oral, ocular or nasal administration or with excipients, such as glycerides or analogous, suitable for the constitution of forms to be administered rectally, or still with gelatinous excipients, for vaginal administration. It also concerns liquid isotonic compositions containing N-acetyl-muramyl-L-alanyl-D-isoglutamine or N-acetyl-muramyl-L-alanyl-D-glutamic acid adapted for administration on ocular or nasal mucous membranes. It finally relates to compositions constituted by liquefied, pharmaceutically acceptable gases, of the "propellent" type in which the N-acetyl-muramyl-L-alanyl-D-isoglutamine or N-acetyl-muramyl-L-alanyl-D-glutamic acid are dissolved or kept in suspension, the expansion of which causes the dispersion of an aerosol.

The invention also relates to a pharmaceutical presentation containing one or several unit doses of N-acetyl-muramyl-L-alanyl-D-isoglutamine or N-acetyl-muramyl-L-alanyl-D-glutamic acid, each dose from about 10 to about 100 mg, preferably 30 mg under lyophilised form, on the one hand, and a corresponding number of ampullae, each containing 1 ml of isotonic solute, for instance chlorinated solute, for the extemporaneous preparation of a dosed solution, more especially for administration by injection, on the other hand.

In the pharmaceutical presentations for administration through oral route, the unit dose of N-acetyl-muramyl-L-alanyl-D-isoglutamine or of N-acetyl-muramyl-L-alanyl-D-glutamic acid is comprised between about 10 and about 200 mg.

Other characteristics if the invention will still appear in the course of the following description of tests evidencing the pharmacological properties of oil-free aqueous solutions containing N-acetyl-muramyl-L-alanyl-D-isoglutamine or N-acetyl-muramyl-L-alanyl-D-glutamic acid and of an example of synthesis of N-acetyl-muramyl-L-alanyl-D-glutamic acid.

It is to be noted that, in the present case, the word oil means fatty substances or analogous in the liquid form at ambient temperatures.

I—PHARMACOLOGY
(Mur-NAc-L-Ala-D-Glu-α-NH$_2$)

(1) Toxicity

The compound according to the invention has been compared with the lipopolysaccharide (LPS) prepared by the phenol-water procedure from *S.enteriditis*, with regard to their lethal doses (LD). The LPS is known to exhibit an adjuvant activity when administered in water solution, but cannot be used as such due to its high toxicity.

The method used to carry out these experiments is described by Chedid and al. in Ann. N.Y. Acad. Sci. 133:712, 1966. The tests are made on two month old Swiss common stock mice. The assayed products are administered by intravenous injections.

The LD$_{50}$ of the LPS is found to be about 300 μg for normal mice. With the very susceptible adrenalectomised mice the LD$_{50}$ is lowered to 0.02 μg.

300 μg of Mur-NAc-L-Ala-D-Glu-α-NH₂ were administered to adrenolectomised mice. All the mice survived this injection.

The product according to the invention is then innocuous at the doses at which it exhibits a good adjuvanticity (these doses are determined in the following tests).

(2) Adjuvanticity in aqueous solution

In these experiments, the antibody levels in mice are determined following the injection of various compositions. The injected compositions contain bovine serum albumin (BSA) as antigen and the adjuvant compound according to the invention. The mice used as controls received the BSA and lipopolysaccharides. The compositions are injected in solution in saline. The injected dose of BSA is 0.5 mg per mouse, the recall dose (30 days after the first injection) contains 0.1 mg of BSA. Each tested composition is administered to eight mice. At various time intervals following the injection, the mice are bled to check the antibody level.

The antibody estimation is made either by passive hemagglutination (PHA) using formalinized sheep red blood cells coated with the tested antigen, or according to the method taught by A. A. Hirata and M. W. Brandiss (J. Immunol., 100, 641–648, 1968), or by the so-called antigen binding capacity method as described by P. Minden and S. Farr (Handbook of Exp. Immunol., p. 463, Weir D. M. ed. Blackwell Scientific Pub., Oxford and Edinburgh, 1967).

Results of these experiments are given in Table 1. As can be seen, the Mur-NAc-L-Ala-D-Glu-α-NH₂ administered in saline induces an enhancement of the antibody titer that can be compared with the one caused by injecting the LPS. As for the primary response is concerned, this titer is even higher.

The tests were repeated to compare the adjuvanticity of the compound according to the invention to those called WSA (water soluble adjuvant) which are prepared from cells of $M.$ $smegmatis$ following the method of A. Adam and al. (Infec. Immun., 7, 855–861, 1973). The same method is described in the French patent application No. 71 41610 filed on Nov. 19, 1971. The results are given in Table 2. From these results, it appears that the WSA in aqueous solution is practically inactive when with the compound according to the invention high antibody titers were observed.

(3) Induced hypersensitivity against various mycobacteria antigens especially tuberculin The capacity of Mur-NAc-L-Ala-D-Glu-α-NH₂ to induce hypersensitivity reaction against various compounds injected with Freund's incomplete adjuvant (FIA) has been studied. For comparison, simultaneous tests were carried out with Freund's complete adjuvant (FCA).

Hartley guinea pigs weighing 350 g are skin-tested. The Mur-NAc-L-Ala-D-Glu-α-NH₂ with FIA or the FCA are injected in the posterior footpad. Eighteen days later, the antigens indicated in Table 3 are injected. Forty-eight hours after this second injection, the diameter of reaction is measured (in mm).

According to the results given in Table 3, no hypersensitivity reaction is observed against FIA neither Mur-NAc-L-Ala-D-Glu-α-NH₂. Thus the Mur-NAc-Ala-D-Glu-α-NH₂ is not immunogenic.

(4) Reaction to influenza virus

The adjuvanticity of the Mur-NAc-L-Ala-D-Glu-α-NH₂ has been studied against the influenza vaccine on mice. The tested animals are injected with the vaccine and the adjuvant compound whereas controls only received the vaccine. Thirty days later, a recall containing only the vaccine is injected.

TABLE 1

| Treatment dose per mouse | Primary response | | | | Secondary response | | | |
|---|---|---|---|---|---|---|---|---|
| | Day 14 | | Day 28 | | Day 34 | | Day 36 | |
| | PHA | ABC | PHA | ABC | PHA | ABC | PHA | ABC |
| Controls BSA | <3 | <20 | <3 | <20 | <3 | <20 | 12 | <20 |
| LPS 30 μg + BSA | <3 | <20 | 6 | <20 | 100 | 120 | 715 | 530 |
| LPS 100 μg + BSA | <3 | <20 | 6 | <20 | 50 | 110 | 1300 | 1600 |
| Mur-NAc-L-Ala-D-Glu-γ-NH₂ 30 μg + BSA | 3 | <20 | 25 | 75 | 200 | 210 | 800 | 400 |
| Mur-NAc-L-Ala-D-Glu-γ-NH₂ 300 μg + BSA | <3 | <20 | 25 | 50 | 200 | 230 | 975 | 550 |

TABLE 2

| Treatment dose per mouse | Day 14 | | Day 28 | | Day 34 | | Day 36 | |
|---|---|---|---|---|---|---|---|---|
| | PHA | ABC | PHA | ABC | PHA | ABC | PHA | ABC |
| Control BSA | <3 | <20 | <3 | <20 | 3 | <20 | 3 | <20 |
| WSA 300 μg + BSA | <3 | <20 | <3 | <20 | 6 | <20 | 6 | 10 65 |
| Mur-NAc-L-Ala-D-Glu-γ-NH₂ 100 μg + BSA | <3 | <20 | 11 25 | 11 82 | 400 | 270 | 2150 | 520 |

TABLE 3

| Treatment per guinea-pig | Skin test | | | |
|---|---|---|---|---|
| | Purified tuberculin 50 IU | Old tuberculin 50 IU | WSA 5 μg | Mur-Nac-L-Ala D-iso-Glu 5 μg |
| FCA | 10,7,10,7,10,7 | 14,10,13,12,13,5 | 6,7,0, 6,3,5, | 0,0,0,0,0,0, |
| FIA+Mur-NAc-L-Ala-D-Glu-γ-NH₂ | 0,0,0,0,0,0, | 0,0,0,0,0,0, | 0,0, 0,0,0, | 0,0,0,0,0,0, |

TABLE 3-continued

| Treatment per guinea-pig | Skin test | | | |
|---|---|---|---|---|
| | Purified tuberculin 50 IU | Old tuberculin 50 IU | WSA 5 μg | Mur-Nac-L-Ala D-iso-Glu 5 μg |
| 50/μg | | | | |

It is to be observed that the antibody level is much higher in animals which have received both vaccine and adjuvant compound than in controls. (The measure is made by hemagglutination inhibition following the method proposed by the World Health Organisation Comitee (1953).)

II—PHARMACEUTICAL FORM

This form is to be used for the extemporaneous preparation of dosed injectable adjuvant solution and contains unit doses of 30 mg lyophilized 2-(2-acetamido-2-deoxy-3-O-D-glucopyranosyl)-D-propionyl-L-alanyl-D-isoglutamine, for each of the above doses an ampoule containing 1 ml of saline (isotonic solution of NaCl).

III—Mur-NAc-L-Ala-D-Glu-(OH) synthesis

This compound, the official name is 2-(2-acetamido-2-deoxy-3-O-D-glucopyranosyl)-D-propionyl-L-alanyl-D-glutamic acid, is prepared stepwise. First, the peptidic moiety is synthesized, then this moiety is bounded to the muramyl moiety; finally, the functions blocked during the synthesis are freed.

BOC-L-alanyl-D-glutamic benzyldiester (I)

2.3 g (8 m moles) of t.butyloxy carbonyl-L-alanin succinimid ester, the amino function of which is protected by the t.butyloxy carbonyl group (BOC-L-Ala-OSu), are added with stirring to a solution in dimethylformamid of 4.5 g (9 m moles) D-glutamic dibenzylester p.toluen sulfonate and of 1 ml (9 m moles) N-methylmorpholine. The mixture remains at room temperature during 12 hours, then evaporated to dryness. The dry compound is dissolved in 50 ml acetic ethyl ester and washed successively with a 10% citric acid solution; water; a 1N sodium bicarbonate solution; water. The acetic ethyl ester part is dried with $MgSO_4$, filtered and concentrated. The compound is crystallized out of a mixture of ethyl acetatehexane, 2.50 g (67.5%) of the desired product are obtained.

M P=105°–106° C.
$a_D^{25} = +7.3°$

The analysis by element is

| $C_{27}H_{34}O_7N_2$ (498,5) | C % | H % | N % |
|---|---|---|---|
| theoretical : | 65 | 6.9 | 5.6 |
| found : | 64.85 | 7.0 | 5.5 |

2-(benzyl-2-acetamido-4,6 benzylidene-2-deoxy-3-O-D-glucopyranosyl)-D-propionyl-(O-benzyl)-L-alanyl-D-glutamic benzyldiester (II)

500 mg (1 m mole) of compound (I) are treated with a 1N hydrochloric solution in glacial acetic acid. Thirty minutes later, the mixture is evaporated to dryness. The oil obtained is dissolved in a mixture of acetonitriledimethylformamid (2/1 v.v.). The mixture is cooled to 0° C. and 0,141 ml (1 m mole) triethylamin is added. This solution is poured with stirring in a dispersion at 0° C. containing 472 mg (1 m mole) of benzyl-2-acetamido-4,6-O-benzylidene-3-O-(D-1 carboxyethyl)-2-deoxy-β-D-glucopyranoside and 0,141 ml (1 m mole) of triethylamine in 25 ml of the mixture acetonitriledimethylformamid (2/1 v.v.).

The mixture remains 12 hours at room temperature, then is concentrated and the residue is poured in a 10% acetic acid solution. The precipitate is filtered, thoroughly washed with water and dried. 800 mg (94%) of the desired product are obtained.

M P=198°–199° C.
$a_D^{25} = 4,92°$ (dimethylformamide)

When the product is crystallized out of ethanol, the melting point is 220° C.

The analysis by element is

| $C_{47}H_{53}O_{12}N_3$ (851,96) | C % | H % | N % |
|---|---|---|---|
| theoretical : | 66.26 | 6.27 | 4.93 |
| found : | 66.34 | 6.45 | 4.92 |

2-(2-acetamido-2-deoxy-3-O-D-glucopyranosyl)-D-propionyl-L-alanyl-D-glutamic acid (III)

700 mg (0.8 m mole) of compound II are treated 1 hour by 40 ml of a 60% acetic acid solution in a boiling waterbath. The mixture is evaporated to dryness (and dessicated with $MgSO_4$). The residue is added to a mixture of chloroformmethanol (3.3 v.v.) and passed through a silica column (35 g) previously contacted with the same solvent mixture. The eluated fractions containing the product are recovered evaporated to dryness (their homogeneity is tested by thin layer chromatography on silicagel with the same mixture of solvents. 185 mg (30%) of intermediate compound are obtained.

76 mg of this intermediate are dissolved in 15 ml of glacial acetic acid and their hydrogenated with 5% palladium on coal as catalyst. The mixture is filtered, evaporated to dryness and precipitated out of an ether-methanol-acetone solvent mixture. 45 mg (92%) of the desired product are obtained.

M P=150°–155° C.
$a_D^{25} = +33°$ (in glacial acetic acid)

The analysis by element is

| $C_{19}H_{31}O_{12}N_3$ $1H_2O$ (511,48) | C % | N % | H % |
|---|---|---|---|
| theoretical : | 44.6 | 6.5 | 8.2 |
| found : | 44.7 | 6.4 | 8.1 |

IV—PHARMACOLOGY
(Mur-NAc-L-Ala-D-Glu(OH))

(1) Toxicity

The compound according to the invention has been compared with the lipopolysaccharide (LPS) prepared by the phenol-water procedure from *S.enteriditis* with regard to their lethal dose (LD). The LPS is known to exhibit an adjuvant activity when administered in water solution, but cannot be used as adjuvant product due to its high toxicity.

Results of these experiments are given in Table A. As can be seen, the Mur-NAc-L-Ala-D-Glu(OH) administered in saline induces an enhancement of the antibody titer, whereas the WSA is practically inactive.

Table A

| Treatment | Day 14 | | Day 28 | | Day 34 | | Day 36 | |
|---|---|---|---|---|---|---|---|---|
| dose/mouse | PHA | ABC | PHA | ABC | PHA | ABC | PHA | ABC |
| Control - BSA | <3 | <20 | <3 | <20 | 3 | <20 | 3 | <20 |
| BSA + WSA 300/μg | <3 | <20 | <3 | <20 | 6 | <20 | 6 | 65 |
| BSA + Mur-Nac-L-Ala-D-Glu(OH) 100/μg | 3 | <20 | 50 | 80 | 400 | 320 | 2,130 | 630 |

The method used to carry out these experiments is described by Chedid and al. in Ann. N.Y. Acad. Sci. 135:712, 1966. The tests are made on two month old Swiss common stock mice. The assayed products are administered by intravenous injection.

The LD$_{50}$ of the LPS is found to be about 300 μg for normal mice. With the very susceptible adrenalectomised mice, the LD$_{50}$ is lowered to 0.02 μg.

300 μg of Mur-NAc-L-Ala-D-Glu(OH) were administered to adrenalectomised mice. All mice survived this injection.

The product according to the invention is then innocuous at the doses at which it exhibits a good adjuvanticity (these doses are determined in the following tests).

(2) Adjuvanticity in aqueous solution

In these experiments, the antibody levels in mice are determined following the injections of various compositions. The injected compositions contain bovine serum albumin (BSA) as antigen and the adjuvant compound according to the invention. Other mice received BSA and the WSA adjuvant compound prepared from *M.smegmatis* according to Adam and al. method (Infec. Immun., 7, 855–861, 1973). The compositions are injected in solution in saline. The injected dose of BSA is 0.5 mg per mouse, the recall dose (30 days after the first injection) contains 0.1 mg of BSA. Each tested composition is administered to eight mice. At various time intervals following the injection, the mice are bled to check the antibody level.

The antibody estimation is made either by passive hemagglutination (PHA) using formalinized sheep red blood cells coated with the tested antigen, or according to method taught by A. A. Hirata and M. W. Brandiss (J. Immunol., 100, 641–648, 1968), or by the so-called antigen binding capacity method described by P. Minden and S. Farr (Handbook of Exp. Immunol., p. 463, Weir D. M. ed. Blackwell Scientific Pub., Oxford and Edinburgh, 1967).

(3) Adjuvanticity with a water in oil emulsion (comparative assay)

As previously, the adjuvanticity is estimated from the increase of the antibody level following an antigen injection. In these experiments, ovalbumin is used as antigen. Assays are carried out on Hartley's guinea pigs weighing 350 g. The animals are injected with 0.1 ml in each posterior footpad. Each dose contains 1 mg ovalbumin and either the Freund's complete adjuvant (FCA) or the Freund's incomplete adjuvant (FIA) or this one with the compound of the invention (50 μg). The antibody titer is estimated 21 days after the injection, by passive hemagglutination as indicated above, or by precipitation according to Folin's method.

A skin test for delayed hypersensitivity is made 18 days after the injection on the same animals. They received 5 μg of ovalbumin by intradermal injection. 48 hours later, the diameter of reaction is measured (in mm).

It can be seen from the results given in Table B that the Mur-NAc-L-Ala-D-Glu(OH), under the condition of this experiment, does not induce an increase of the antibody titer when injected with the oil constituted by the Freund's incomplete adjuvant. The skin test reaction is light compared with the one obtained with the Freund's complete adjuvant (FCA).

Table B

| Treatment | Skin test | Antibody a. ovalbumin | |
|---|---|---|---|
| dose/guinea-pig | Ovalbumin 5/μg | Precipitin | Agglutinin |
| FIA (controls) + ovalbumin | 0,0,0,0,0,0 | 500 | 1,000 |
| FCA + ovalbumin | 10,8,10,12,11 | 3,200 | 2,400 |
| FIA + Mur-NAc-L-Ala-D-Glu(OH) 50/μg + ovalbumin | | | |

(4) Induced hypersensitivity against various mycobacteria antigens especially tuberculin The capacity of Mur-NAc-L-Ala-D-Glu(OH) to induce hypersensitivity reaction against various compounds injected with Freund's incomplete adjuvant (FIA) has been studied. For comparison, simultaneous tests were carried out with Freund's complete adjuvant (FCA).

The estimation is made as previously described.

According to the results given in table C, no hypersensitivity reaction is observed against FIA+Mur-NAc-L-Ala-D-Glu(OH). Thus the Mur-NAc-L-Ala-D-Glu(OH) is not immunogenic.

Table C

| Treatment dose/guinea-pig | Skin test | | | |
|---|---|---|---|---|
| | Purified tuberculin 50 IU | Old tuberculin 50 IU | WSA 5/µg | Mur-NAc-L-Ala-D-Glu(OH) 5/µg |
| FCA | 10,7,10,7,10,7 | 14,10,13,12,13,5 | 6,7,0,6,3,5 | 0,0,0,0,0,0 |
| FIA+Mur-NAc-L-Ala-D-Glu(OH) 50/µg | 0,0,0,0,0,0 | 0,0,0,0,0,0 | 0,0,0,0,0,0 | 0,0,0,0,0,0 |

V—PHARMACEUTICAL FORM

This form is to be used for the extemporaneous preparation of dosed injectable adjuvant solution and contains:

unit doses of 30 mg lyophilized 2-(2-acetamido-2-deoxy-3-O-D-glucopyranosyl)-D-propionyl-L-alanyl-D-glutamic acid, for each of the above doses an ampoule containing 1 ml of saline (isotonic solution of NaCl).

Thus, oil-free adjuvant compositions are obtained which are deprived of toxicity or noxious secondary effects and, therefore, particularly proper for therapeutical applications.

Adjuvant compositions are obtained, which may be used to increase the efficiency of vaccines of bacterial or viral origin, more especially if they are light immunogens. More especially, they may be used to increase the host's immunity (either human or animal) against infections of bacterial or viral origin, tumor antigens, protozoa antigens, esw. They are also useful for making serums containing active antibodies against said antigens.

We claim:

1. An adjuvant composition comprising an effective amount of N-acetyl muramyl-L-alanyl-D-isoglutamine and a pharmaceutically acceptable carrier, which composition is oil-free.
2. The aqueous solution of the composition of claim 1.
3. The solution of claim 2 which is free of mineral salts.
4. The solution of claim 2 which is isotonic.
5. The solution of claim 4 which is sterile.
6. The solution of claim 2 which is injectable.
7. The composition of claim 1 which comprises in addition a vaccinating antigen.
8. The composition of claim 1 which is lyophylized.
9. The composition of claim 8 which comprises in addition a vaccinating antigen.
10. The composition of claim 7 wherein the carrier is a solid.
11. The composition of claim 10 which is suitable for oral administration.
12. The composition of claim 10 which is suitable for rectal administration.
13. The composition of claim 1 in suspension form in a liquified propellant type gas.
14. The composition of claim 9 which is suitable for vaginal administration.
15. The composition of claim 7 which is suitable for nasal, ocular or vaginal local administration.
16. The composition of claim 1 wherein the N-acetyl muramyl-L-alanyl-D-isoglutamine is present in the range from about 10 to about 200 mg.
17. The composition of claim 16 wherein the range is from about 30 to about 100 mg.
18. The composition of claim 16 which is an injectable isotonic sodium chloride solution.
19. The process which comprises treating a subject with the composition of claim 1 to increase the production of circulating antobides in vivo without developing a sensitizing reaction in the subject.
20. The process of claim 19 wherein the subject has previously been exposed to at least one adjuvant selected from the group consisting of N-acetyl muramyl-L-alanyl-D-isoglutamine, mycobacteria or mycobacterial extracts, or an adjuvant extractable from mycobacteria or Nocardia.
21. The process of claim 19 wherein the composition is a solution.
22. The process of claim 19 wherein the composition is a reconstituted lyophilisate.
23. The process of claim 19 wherein the composition is used in an amount sufficient to have a non-specific adjuvant effect.
24. The composition of claim 9 wherein the antigen is a weak immunogen.
25. The method of claim 23 wherein the administration is oral.
26. The method of claim 23 wherein the administration is in a pharmaceutically acceptable aerosol.
27. A physiologically active composition which comprises an effective amount of N-acetyl-muramyl-L-alanyl-D-isoglutamine in a physiological serum free of oil.
28. A physiologically active composition which comprises an effective amount of N-acetyl-muramyl-L-alanyl-D-isoglutamine in a physiological aqueous glucose solution free of oil.
29. A method for stimulating an immune response in a host which comprises administering to the host an effective amount of a composition free of oil comprising N-acetyl-muramyl-L-alanyl-D-isoglutamine and an antigen, thereby increasing the production of circulating antibodies in vivo.
30. The method of claim 29 wherein the administration is performed in conjunction with the administration of a vaccine to the host.
31. A therapeutic method for stimulating an immune response in a host without causing an immunogenic reaction in the host, which comprises administering to the host an effective amount of a composition free of oil comprising N-acetyl-muramyl-L-alanyl-D-isoglutamine and a carrier.

* * * * *